US012712353B2

(12) United States Patent
Hancock et al.

(10) Patent No.: US 12,712,353 B2
(45) Date of Patent: Aug. 18, 2026

(54) INTERFACE JOINT FOR AN ELECTROSURGICAL APPARATUS

(71) Applicant: CREO MEDICAL LIMITED, Chepstow (GB)

(72) Inventors: Christopher Paul Hancock, Chepstow (GB); George Christian Ullrich, Anglesey (GB)

(73) Assignee: CREO MEDICAL LIMITED, Chepstow (GB)

( * ) Notice: Subject to any disclaimer, the term of this patent is extended or adjusted under 35 U.S.C. 154(b) by 146 days.

(21) Appl. No.: 18/700,091

(22) PCT Filed: Oct. 11, 2022

(86) PCT No.: PCT/EP2022/078280
§ 371 (c)(1),
(2) Date: Apr. 10, 2024

(87) PCT Pub. No.: WO2023/066729
PCT Pub. Date: Apr. 27, 2023

(65) Prior Publication Data

US 2024/0348034 A1 Oct. 17, 2024

(30) Foreign Application Priority Data

Oct. 18, 2021 (GB) ..................................... 2114861

(51) Int. Cl.
*H02G 15/08* (2006.01)
*A61B 1/018* (2006.01)
(Continued)

(52) U.S. Cl.
CPC ........... *H02G 15/085* (2013.01); *A61B 1/018* (2013.01); *A61B 18/1206* (2013.01); *A61B 18/1492* (2013.01)

(58) Field of Classification Search
None
See application file for complete search history.

(56) References Cited

U.S. PATENT DOCUMENTS

2013/0126207 A1 5/2013 Rossetto et al.
2018/0036081 A1 2/2018 Dickhans et al.
(Continued)

OTHER PUBLICATIONS

Search Report Under Section 17(5), issued by the United Kingdom Intellecutal Property Office in corresponding United Kingdom Application No. GB2114861.4, dated Jul. 4, 2022.
(Continued)

*Primary Examiner* — Rochelle D Turchen
(74) *Attorney, Agent, or Firm* — ArentFox Schiff LLP

(57) ABSTRACT

The present invention relates to an interface joint for interconnecting an electrosurgical generator and an electrosurgical instrument. In particular, the invention relates to an interface joint comprising a coaxial cable assembly for connecting the interface joint to an electrosurgical instrument. The interface joint comprises a housing made of electrically insulating material, the housing having: an inlet for receiving radiofrequency (RF) electromagnetic (EM) energy and/or microwave frequency EM energy from the electrosurgical generator, and an outlet; and a coaxial cable assembly for connecting the outlet to the electrosurgical instrument, the coaxial cable assembly comprising a first cable section and a second cable section, wherein the first cable section has a lower loss per unit length than the second cable section.

17 Claims, 3 Drawing Sheets

(51) Int. Cl.
*A61B 18/12* (2006.01)
*A61B 18/14* (2006.01)

(56) References Cited

U.S. PATENT DOCUMENTS

| | | | |
|---|---|---|---|
| 2020/0008872 | A1 | 1/2020 | Hancock et al. |
| 2021/0113261 | A1 | 4/2021 | Eaton-Evans et al. |
| 2021/0236202 | A1 | 8/2021 | Allison et al. |

OTHER PUBLICATIONS

International Search Report and Written Opinion, issued by the International Searching Authority in corresponding International Patent Application No. PCT/EP2022/078280, dated Feb. 7, 2023.

INTERFACE JOINT FOR AN ELECTROSURGICAL APPARATUS

CROSS-REFERENCE TO RELATED APPLICATIONS

This application is a National Stage Entry of International Application No. PCT/EP2022/078280, filed Oct. 11, 2022, which claims priority to United Kingdom Patent Application No. 2114861.4, filed Oct. 18, 2021. The disclosures of the priority applications are hereby incorporated in their entirety by reference.

FIELD OF THE INVENTION

The present invention relates to an interface joint for interconnecting an electrosurgical generator and an electrosurgical instrument. In particular, the invention relates to an interface joint comprising a coaxial cable assembly for connecting the interface joint to an electrosurgical instrument. The invention may find particular use in endoscopic procedures, such as gastrointestinal (GI) procedures associated with the upper and lower GI tract, e.g. to remove polyps on the bowel, i.e. for endoscopic mucosal resection, or endoscopic submucosal dissection.

BACKGROUND

Electrosurgical generators are prevalent in hospital operating theatres, often for use in open and laparoscopic procedures, and increasingly for use in endoscopy suits. In endoscopic procedures an electrosurgical accessory is typically inserted through a lumen inside an endoscope. Considered against the equivalent access channel for laparoscopic surgery, such a lumen is comparatively narrow in bored and greater in length.

Instead of a sharp blade, it is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. In practice, an instrument is arranged to apply an RF voltage across the tissue matrix that is sufficient to generate heat within the cells to vaporise the water content of the tissue. However, as a result of this increasing desiccation, particularly adjacent to the RF emitting region of the instrument (which has the highest current density of the current path through tissue), direct physical contact between the tissue and instrument can be lost. The applied voltage then manifests itself as a voltage drop across this small void, which causes ionisation in the void that leads to a plasma. Plasma has a very high volume resistivity compared with tissue. The energy supplied to the instrument maintains the plasma, i.e. completes the electrical circuit between the instrument and the tissue. Volatile material entering the plasma can be vaporised and the perception is therefore of a tissue dissecting plasma. In other arrangements, it is common to use microwave frequency energy to cut tissue or perform coagulation using an electrosurgical accessory.

In order to deliver energy from a generator to an electrosurgical accessory, a coaxial cable is used. As noted above, the lumen through which the electrosurgical accessory is inserted will typically be quite narrow, and in order to allow rotation of the device as well as easy insertion through the channel, the electrosurgical accessory and coaxial cable will need to have a smaller diameter than this lumen. Thus, the small diameter of the lumen leads to a smaller coaxial cable being used, which leads to high insertion losses as well as cable heating along the length of the shaft. For example, a coaxial cable having an outer diameter of 1.02 mm can have an insertion loss of around 3 dB/m, which means that half of the power is lost for each metre of the cable which is used. Considering that endoscopes can be in excess of 1.5 m long in some cases, this leads to appreciable losses.

The present invention has been devised in light of the above considerations.

SUMMARY OF THE INVENTION

According to a first aspect of the present invention, there is provided an interface joint for interconnecting an electrosurgical generator and an electrosurgical instrument, the interface joint comprising: a housing made of electrically insulating material, the housing having: an inlet for receiving radiofrequency (RF) electromagnetic (EM) energy and/or microwave frequency EM energy from the electrosurgical generator, and an outlet; and a coaxial cable assembly for connecting the outlet to the electrosurgical instrument, the coaxial cable assembly comprising a first cable section and a second cable section, wherein the first cable section has a lower loss, or attenuation, per unit length than the second cable section. In particular, the first cable section may be a proximal cable section, and the second cable section may be a distal cable section. The coaxial cable assembly conveys RF and/or microwave frequency energy from the outlet to the electrosurgical instrument. Both the first section and the second section of the coaxial cable assembly comprise an inner conductor, an outer conductor coaxial with the inner conductor, and a dielectric material separating the inner and outer conductors. The first cable section and the second cable section may be connected by any suitable means, for example QMA or SMA connectors, or any means described herein. By being configured in this way, the invention is able to reduce losses in energy conveyed from a generator to an electrosurgical instrument. In particular, by being arranged in this way, the first section of the coaxial cable assembly can be optimised to reduce power losses, and the second section of the coaxial cable assembly can be optimised for insertion through the working channel of an endoscope to an electrosurgical instrument. The first section of the coaxial cable may also have other adaptations which allow it to be particularly suitable for rotation by an operator of an electrosurgical system, and delivering rotation to the distal end of the coaxial cable assembly. Furthermore, as the first section of the coaxial cable assembly has a larger diameter, this results in reduced heating of that section as energy is delivered through the coaxial cable assembly. This may make the coaxial cable assembly easier to handle, for example when moving rotating the coaxial cable assembly at the proximal end.

Each section of the coaxial cable assembly comprises an inner conductor, an outer conductor coaxial with the inner conductor, and a dielectric material separating the inner and outer conductors. Preferably, the first cable section may have a larger diameter than the second cable section. In particular, this may help to ensure that resistive losses (in particular, skin effect resistance) in the first cable section are reduced due to the larger outer diameter of the inner conductor and the larger inner diameter of the outer conductor of the first cable section, while the second cable section is easily insertable through the working channel of an endoscope. In addition, such an arrangement allows for easier rotation of an electrosurgical instrument at the distal end of the coaxial cable assembly, as the first cable section is easier to rotate and more effectively delivers the rotation along its length. Twisting or bending a coaxial cable can have a negative effect by increasing losses in the cable due to flexing and damage of shielding within the cable. However, by using a first coaxial cable section with a larger diameter, such negative effects can be reduced or minimised. For example, the first cable section may have a diameter of at least 2 mm, preferably at least 5 mm, or more than 10 mm. In embodiments, the second cable section may have a diameter of less than 10 mm, for example less than 5 mm, preferably less than 2 mm. It will be appreciated that when the diameter of a coaxial cable or coaxial cable section is referred to herein, this should be understood as referring to the outer diameter of the outer conductor of the coaxial cable unless specified otherwise. It will be appreciated that the thickness of the outer conductor may also be relevant for calculating loss/attenuation and when considering cable impedance as discussed below.

Advantageously, the first cable section and the second cable section are coupled together by a transition portion, wherein the transition portion comprises a tapering section of coaxial cable. In particular, the first cable section is connected to the transition portion at a proximal side thereof, and the second cable section is connected to the transition portion at a distal side thereof, such that the first and second sections are coupled together. In this way, it can be ensured that the first cable section and the second cable section are strongly connected together and that any rotation of the first cable section will be efficiently transferred to rotation of the second cable section.

Preferably, the ratio of the inner diameter of the outer conductor to the outer diameter of the inner conductor is constant through the tapering section. This ensures good impedance matching between the first cable section and the second cable section and minimises reflection at the interface between the first cable section and the transition portion, and the interface between the transition portion and the second cable section. For example, the first cable section and the second cable section may each have an impedance of 50Ω, and the ratio of the inner diameter of the outer conductor to the outer diameter of the inner conductor may be constant through the tapering section in order to maintain this impedance.

The impedance ($Z_0$) of a coaxial cable is dependent on the dielectric constant (relative permittivity, $\varepsilon_r$) of the dielectric material separating the inner conductor and outer conductor, as well as the inner diameter of the outer conductor ($D_{outer}$) and outer diameter of the inner conductor ($d_{inner}$), as shown in the following formula $$Z_0 = \frac{138}{\sqrt{\varepsilon_R}} \log_{10}\left(\frac{D_{outer}}{d_{inner}}\right).$$

From this equation, the ratio of the inner diameter of the outer conductor to the outer diameter of the inner conductor may be shown by $$\frac{D_{outer}}{d_{inner}} = 10^{\frac{Z_0\sqrt{\varepsilon_R}}{138}}.$$

In an example where the impedance of the coaxial cable is 50Ω, and the relative permittivity of the dielectric material is 2.2 (for example where the dielectric is PTFE, such as aerated PTFE), the ratio of the inner diameter of the outer conductor to the outer diameter of the inner conductor is approximately 3.45:1. Preferably, this ratio is maintained throughout the length of the coaxial cable assembly. Any suitable dimensions of the inner conductor and the outer conductor may be chosen which satisfy this relationship.

Preferably, the length of the tapering section may be no more than one eighth of the wavelength of the EM energy which is received from the electrosurgical generator. This may also help ensure good impedance matching between the first cable section and the second cable section and minimise reflection at the interface between the first cable section and the second cable section.

Optionally, the first cable section and the second cable section may be coupled together by a microstrip transmission line. In particular, the first cable section is connected to the microstrip transmission line at a proximal side thereof, and the second cable section is connected to the microstrip transmission line at a distal side thereof, such that the first and second sections are coupled together. For example, a suitable microstrip transmission line may comprise a planar dielectric material having a conductive strip on an upper surface, and a conductive ground plane on an opposing lower surface. Providing a coaxial cable assembly wherein the first cable section and the second cable section are connected by a microstrip in this way may be easier and cheaper to manufacture than other arrangements. Preferably, the microstrip transmission line is configured to match the impedance of the first cable section and the second cable section to minimise reflections and losses between the two cable sections. For example, the width and/or thickness of an upper conductor of the microstrip and/or the width and/or thickness of a lower conductor (or ground plane) may be adjusted to achieve the impedance matching. For example, the first cable section and the second cable section may each have an impedance of 50Ω, and the microstrip transmission line may be configured to maintain this impedance.

The impedance ($Z_0$) of a microstrip transmission line is dependent on the dielectric constant (relative permittivity, $\varepsilon_r$) and thickness (h) of the planar dielectric material, the width (w) and thickness (t) of the conductive strip formed on the upper surface of the planar dielectric material, as shown in the following formula $$Z_0 = \frac{87}{\sqrt{\varepsilon_r + 1.41}} \ln\left(\frac{5.98 \times h}{0.8 \times w + t}\right).$$

Any suitable dimensions of the various components may be chosen according to the above formula to give the microstrip transmission line an impedance of 50Ω in order to match the impedances of the first cable section and the second cable section.

Preferably, the interface joint may further comprise an outer shaft about the coaxial cable assembly and defining a passageway, or lumen, between the outer shaft and the coaxial cable assembly. For example, the outer shaft may enclose the coaxial cable assembly along its length. The coaxial cable assembly preferably comprises an insulating jacket over the outer conductors of the first cable section and the second cable section in such embodiments. The passageway defined between the outer shaft and the cable assembly may thereby allow for fluid delivery along the length of the cable assembly in some examples. Additionally or alternatively, the passageway may be used to convey actuation wires or cables along the length of the cable assembly. For example, actuation wires may pass to an electrosurgical instrument connected to the distal end of the coaxial cable assembly, and may be used to actuate or operate parts of the electrosurgical instrument (for example, opening and closing jaws or the like).

According to a second aspect of the invention, there is provided an electrosurgical apparatus comprising: an electrosurgical generator configured to generate radiofrequency (RF) electromagnetic (EM) energy and/or microwave frequency EM energy; an electrosurgical instrument configured to deliver RF and/or microwave frequency EM energy to tissue; an interface joint according to the first aspect of the invention; and an interface cable configured to deliver RF and/or microwave frequency EM energy from the electrosurgical generator to the interface joint. In particular, the interface cable may be connectable to the electrosurgical generator at a first end and to the inlet of the interface joint at a second end. The electrosurgical instrument may be connectable to a distal end of the coaxial cable assembly of the interface joint. In this way, the second aspect of the invention provides an electrosurgical apparatus in which losses between the generator and the electrosurgical instrument can be reduced.

Preferably the electrosurgical apparatus further comprises a surgical scoping device having an instrument channel for receiving at least a portion of the coaxial cable assembly, e.g. for delivering an electrosurgical instrument to a treatment location. In some embodiments, only the second cable section of the coaxial cable assembly is configured to be received within the instrument channel. The first coaxial cable section may be located entirely outside the instrument channel. For example, the first section of the coaxial cable assembly can be optimised to reduce power losses, and the second section of the coaxial cable assembly can be optimised to be inserted through the working channel of the surgical scoping device, for example by having increased flexibility compared with the first coaxial cable section, or by having a length which is suitable for reaching a treatment location. In some examples, an outer diameter of the first cable section may be greater than a diameter of an instrument channel of the surgical scoping device, which prevents the first cable section from entering the instrument channel but allows reduced power losses. A surgical scoping device may be an endoscope, a bronchoscope, a colonoscope, or any other kind of surgical scoping device. Advantageously, the length of the second cable section is at least the same as the length of an instrument channel of the surgical scoping device.

Herein, radiofrequency (RF) may mean a stable fixed frequency in the range 10 kHz to 300 MHz and microwave frequency may mean a stable fixed frequency in the range 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz. Preferred spot frequencies for the microwave energy include 915 MHz, 2.45 GHz, 5.8 GHz, 14.5 GHz, 24 GHz. Herein, the terms “proximal” and “distal” refer to the ends of the energy conveying structure further from and closer to the treatment site respectively. Thus, in use the proximal end is closer to a generator for providing the EM energy, whereas the distal end is closer to the treatment site, i.e. the patient, or towards the electrosurgical instrument.

The invention includes the combination of the aspects and preferred features described except where such a combination is clearly impermissible or expressly avoided.

SUMMARY OF THE FIGURES

Embodiments and experiments illustrating the principles of the invention will now be discussed with reference to the accompanying figures in which.

DETAILED DESCRIPTION OF THE INVENTION

Aspects and embodiments of the present invention will now be discussed with reference to the accompanying figures. Further aspects and embodiments will be apparent to those skilled in the art. All documents mentioned in this text are incorporated herein by reference.

Figure 1:
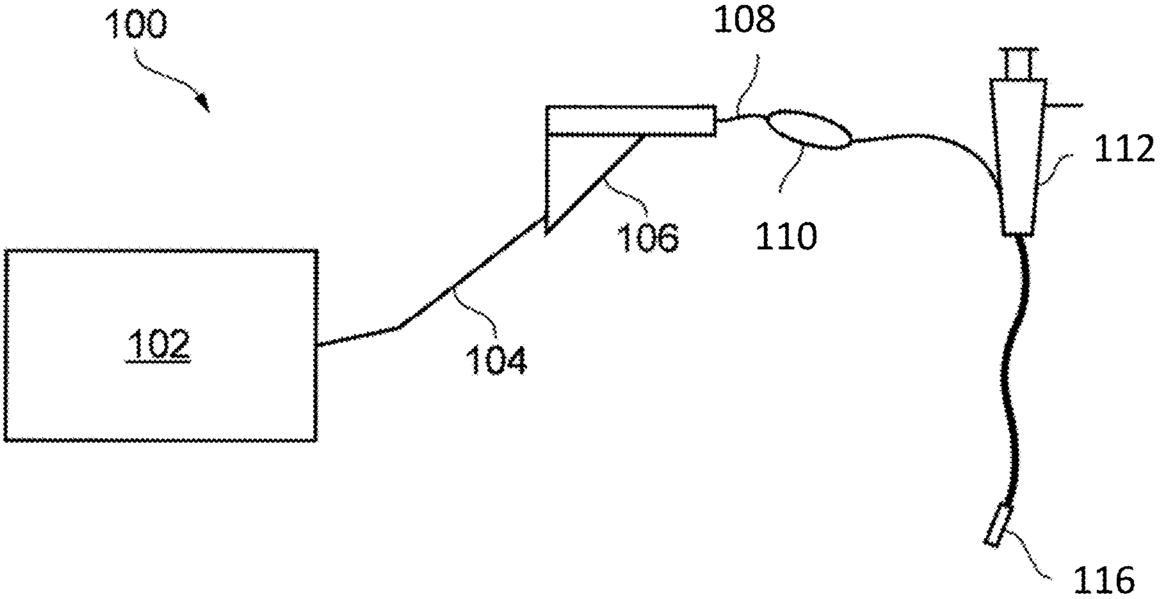
FIG. 1. is a schematic view of an electrosurgical system according to an embodiment of the present invention.

FIG. 1 is a schematic diagram of an electrosurgical system 100 according to an embodiment of the present invention. The electrosurgical system is capable of selectively supplying RF energy and/or microwave energy to the distal end of an invasive electrosurgical instrument. The system 100 comprises a generator 102 for controllable supplying RF electromagnetic (EM) energy and/or microwave frequency EM energy. A suitable generator for this purpose is described in WO 2012/076844, which is incorporated herein by reference.

The generator 102 is connected to an interface joint 106 by an interface cable 104. The interface joint 106 provides a handpiece which may be held by an operator of the system 100, for example when performing surgery. The interface joint 106 may, in some examples, be adapted to receive a fluid supply and house one or more control mechanisms for the electrosurgical instrument (e.g. rotation, longitudinal movement, needle movement mechanism), and combine these inputs into a single shaft extending from the distal end of the interface joint 106.

In accordance with the present invention, a coaxial cable assembly 108 extends from the distal end of the interface joint 106 from an outlet thereof. As will be described in more detail below, the coaxial cable assembly 108 comprises a first cable section and a second cable section. The coaxial cable assembly 108 is insertable through the entire length of an instrument (working) channel of an endoscope 112. A torque transfer unit 110 is mounted on a proximal length of the coaxial cable assembly 108 between the interface joint 106 and the endoscope 112. The torque transfer unit 110 engages the coaxial cable assembly 108 to permit it to be rotated within the instrument channel of the endoscope 112.

At the distal end of the coaxial cable assembly 108 there is an electrosurgical instrument 116 that is shaped to pass through the instrument channel of the endoscope 112 and protrude (e.g. inside the patient) at the distal end of the endoscope’s tube. The electrosurgical instrument 116 includes an active tip for delivering RF EM energy and/or microwave EM energy into biological tissue. In some examples the instrument 116 may include a retractable hypodermic needle for delivering fluid. In this way the electrosurgical instrument 116 is adapted for cutting and destroying unwanted tissue and the ability to seal blood vessels around the targeted area. Through use of the retractable hypodermic needle, the surgeon is able to inject saline and/or hyaluronic acid with added marker dye between tissues layers in order to distend and mark the position of a lesion to be treated. The injection of fluid in this manner lifts and separates the tissue layers making it both easier to resect around the lesion and plane through the submucosal layer, reducing the risk of bowel wall perforation and unnecessary thermal damage to the muscle layer.

The structure of the electrosurgical instrument 116 may be particularly designed for use with a conventional steerable flexible endoscope having a working channel with an internal diameter of at least 2.8 mm and a channel length of between 60 cm and 170 cm. As such the majority of the comparatively small diameter (less than 3 mm) instrument is housed within the lumen of a much larger and predominantly polymer insulating device, i.e. the flexible endoscope channel, which typically has an outer diameter of 11 mm to 13 mm. In practice, only 15 mm to 25 mm of the distal assembly protrudes from the distal end of the endoscope channel, in order not to block the field of view or adversely affect camera focusing. The protruding part of the distal assembly is the only portion of the instrument that ever makes direct contact with the patient.

At the proximal end of the endoscope working channel, which is typically held 50 cm to 80 cm from the patient, the coaxial cable assembly 108 emerges from the working channel port and extends a further 30 cm to 100 cm to the interface joint 106. In use, the interface joint 106 is typically held by a gloved assistant throughout the procedure. The interface joint 106 is designed and manufactured from polymer materials in such a way as to provide primary and secondary electrical insulation with extended creepage and clearance distances. The interface cable 104 is connected to the generator 102 using a QMA-type coaxial interface, which is designed to allow continuous clockwise or counter clockwise rotation. This permits the interface joint 106 to rotate with the torque transfer unit 110 under the control of the endoscopist. The assistant supports the interface joint 106 throughout the procedure in order to assist the endoscopist with sympathetic instrument rotation, and needle control, fluid injection where applicable.

Figure 2:
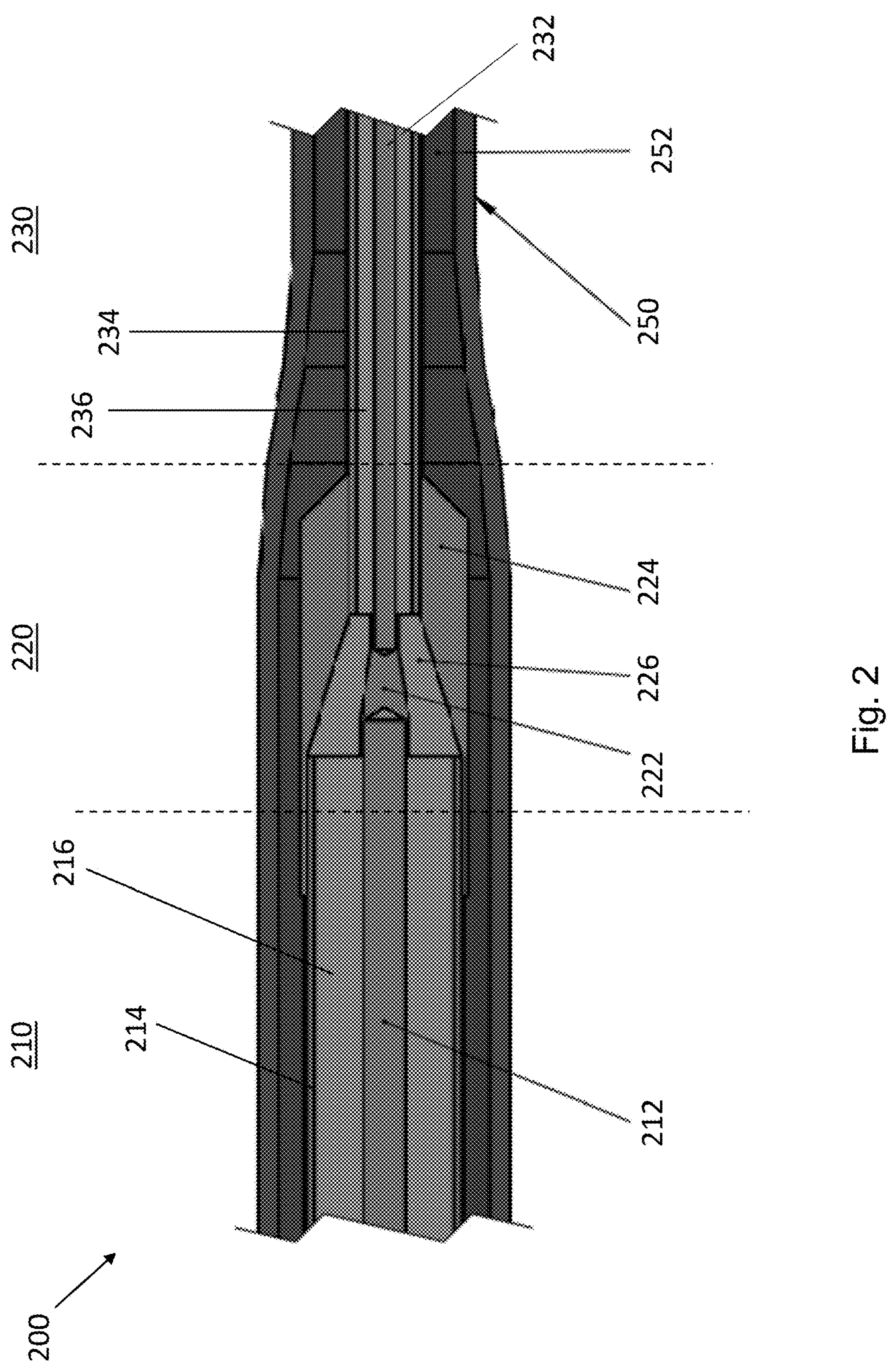
FIG. 2. is a cross-sectional view of a coaxial cable assembly which may be used in embodiments of the present invention.

FIG. 2 shows a cross-section view through a coaxial cable assembly 200 which may be used in embodiments of the present invention. For example, the coaxial cable assembly 200 may be used in the electrosurgical assembly 100 described above with respect to FIG. 1. The coaxial cable assembly 200 comprises a first cable section 210, a second cable section 230, and a transition portion 220.

The first cable section 210 comprises an inner conductor 212, an outer conductor 214 which is disposed coaxially with respect to the inner conductor 212, and a dielectric material 216 which is disposed coaxially between the inner conductor 212 and the outer conductor 214. The dielectric material 216 has a dielectric constant of 2.2. In this embodiment, the first cable section 210 has an outer diameter of 2.3 mm, though it will be appreciated that any suitable diameter of coaxial cable may be used. The first cable section 210 extends from an interface joint at its proximal end, and is configured to convey RF and/or microwave frequency EM energy for electrosurgery. The inner diameter of the outer conductor 214 is around 2 mm, and the outer diameter of the inner conductor 212 is around 0.58 mm, such that the impedance of the first cable section 210 is 50Ω.

The second cable section 230 also comprises an inner conductor 232, an outer conductor 234 coaxial with the inner conductor 232, and a dielectric material 236 between the inner conductor 232 and the outer conductor 234. The dielectric material 236 has a dielectric constant of 2.2. However, the diameter of the second cable section 230 is less than that of the first cable section 210. For example, in this embodiment the second cable section 230 has an outer diameter of 1.1 mm, though of course any suitable diameter of coaxial cable may be used. The inner diameter of the outer conductor 234 is around 0.8 mm, and the outer diameter of the inner conductor 232 is around 0.23 mm, such that the impedance of the second cable section 230 is 50Ω, matching the impedance of the first cable section 210.

As a result of having a lower diameter, the second cable section 230 has a higher loss, or attenuation, per unit length (e.g. per metre) than the first cable section 210. The second cable section 230 is configured to connect to an electrosurgical instrument, such as a radiating tip in the form of a RF and/or microwave antenna, for treating tissue at its distal end. The diameter of the second cable section 230 is therefore chosen to allow the second cable section 230 to be inserted through the working channel of a scoping device (such as an endoscope) to reach a treatment site. In addition, the length of the second cable section 230 should therefore be at least the same length as the instrument channel of the scoping device. As explained above with respect to FIG. 1, in practice only 15 mm to 25 mm of the distal assembly protrudes from the distal end of the endoscope channel, and so the length of the second cable section 230 is preferably no more than around 30 mm longer than the length of the working channel to allow for this protrusion. For example, a typical working channel may have a length of between 60 cm and 170 cm, and so a corresponding length of the second cable section 230 may be at least 60 cm (for example 63 cm to allow for protrusion of the instrument at the distal end) up to at least 170 cm (for example 173 cm). Of course, it will be appreciated that the length of the second cable section 230 which is appropriate will depend on the length of the instrument channel and the intended use for the radiating tip, as well as the desired extent to which the electrosurgical tip should protrude from the distal end of the working channel.

As the first cable section 210 is not required to be inserted through the working channel of a scoping device, the first cable section 210 can have a larger diameter and hence lower loss. This reduces losses in energy delivered to a distal tip compared to an arrangement wherein the entire length of the coaxial cable between the interface joint and the distal tip has the same diameter which is suitable for insertion through a working channel. Although in the depicted embodiment the first cable section 210 has an outer diameter of 2.3 mm, it will be appreciated that the first cable section 210 could have a larger outer diameter, for example at least 5 mm, to further reduce losses in this section of the coaxial cable assembly 200.

To connect the first cable section 210 and the second cable section 230, the coaxial cable assembly 200 comprises a transition portion 220, wherein the transition portion 220 comprises a tapering section of coaxial cable. The transition portion 220 comprises an inner conductor 222 which is connected at its proximal end to the inner conductor 212 of the first cable section 210 and is connected at its distal end to the inner conductor 232 of the second cable section 232. The inner conductor 222 of the transition portion 220 is a tapering length of conductive material (e.g. metal) the outer diameter of which reduces in the proximal-to-distal direction (that is, in the direction from the first cable section 210 to the second cable section 230). Surrounding the inner conductor 222, the transition portion 220 comprises a dielectric material 226, connected to the dielectric material 216 of the first cable section 210 at its proximal end and connected to the dielectric material 236 of the second cable section 230 at its distal end, and which also tapers in the proximal-to-distal direction. Preferably, the dielectric material 226 is the same as the material used in the first cable section 210 and the second cable section 230. Outside of the dielectric material 225 there is an outer conductor 224, similarly connected at its proximal end to the outer conductor 224 of the first cable section 210 and at its distal end to the outer conductor 234 of the second cable section 230. As with the inner conductor 222 and the dielectric material, the outer conductor 234 tapers in the proximal-to-distal direction, in particular the inner surface of the outer conductor 234 tapers as shown in FIG. 2.

To help ensure that energy is efficiently passed through the coaxial cable assembly 200, the transition portion 220 is configured to match the impedance of the first cable section 210 and the second cable section 220. In particular, the ratio of the inner diameter of the outer conductor 224 to the outer diameter of the inner conductor 222 is maintained throughout the transition portion 220, as the inner conductor 222 and the outer conductor 224 taper in the distal direction in order to connect the larger diameter first cable section 210 to the smaller diameter second cable section 230. In addition, the length of the tapering section in the transition portion 220 may also be adapted to ensure good impedance matching, and hence reduce reflection of energy at the interface between the first cable section 210 and the third cable section 230, and in particular the respective interfaces between the first cable section 210 and the transition portion 220, and between the interface portion 220 and the third cable section 230. In particular, the length of the tapering section of the transition portion 220 is no more than one eighth of the wavelength of EM energy which is delivered through the coaxial cable assembly 200. For example, assuming microwave EM energy having a frequency of 5.8 GHz is delivered through the cable assembly 200, and the dielectric material 226 has a dielectric constant of 2.2, then the length of the tapering section should be less than 4.36 mm, as $$\lambda = \frac{c}{f\sqrt{\epsilon_R}},$$

where λ is the signal wavelength, c is the speed of light, f is the signal frequency and $\varepsilon_{R\ is\ the}$ dielectric constant of the dielectric material 226.

The coaxial cable assembly 200 further comprises an outer shaft 250 which encloses the coaxial cable assembly 200 along its length. The outer shaft 250 is made of an insulating material, such as a plastics material. The outer shaft 250 is spaced apart from the coaxial cable assembly 200, for example by using spacer elements or struts, in order to define a lumen or passageway 252 outside of the coaxial cable assembly 200. The outer shaft 250 also tapers in the region of the transition portion 220. This passageway 252 may be used as a fluid flow path to convey fluid through the working channel of the endoscope to the treatment region, or it may be used for conveying actuation wires or other actuation devices which may be used to control functions of the surgical tip (e.g. for movement of the distal tip).

Preferably the outer shaft 250 is torque stable in order to help in conveying rotation of the coaxial cable assembly 200 from the proximal end to the distal end.

Figure 3A:
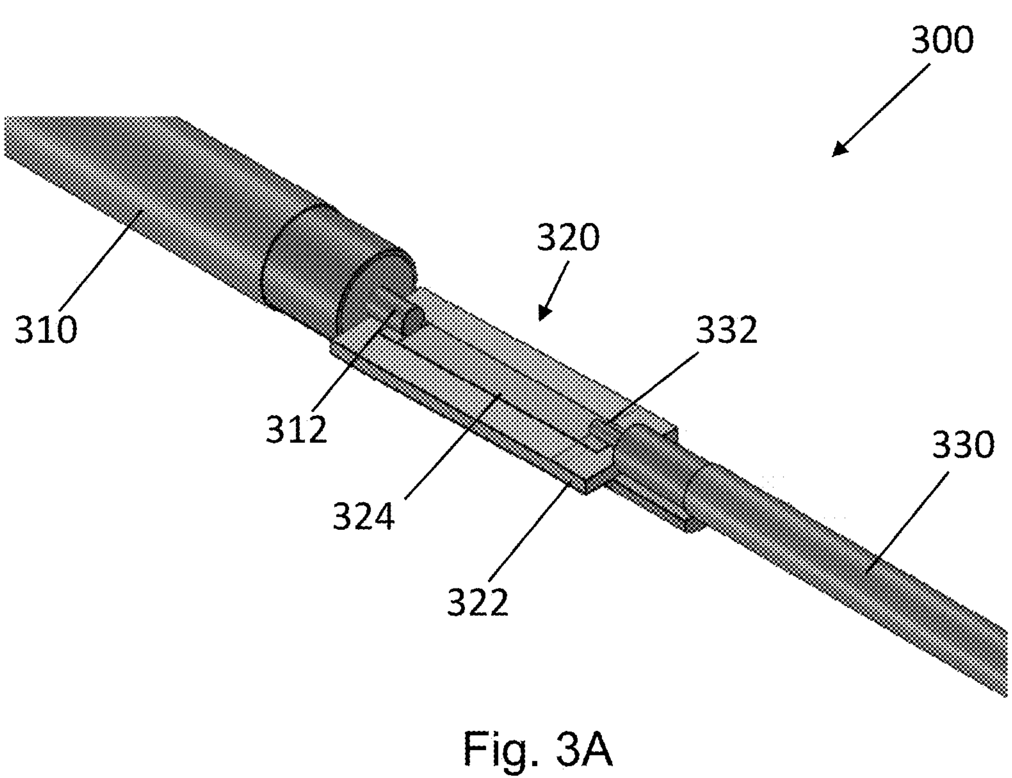
FIGS. 3A and 3B are perspective views showing the upper side and the lower side, respectively, of another coaxial cable assembly which may be used in embodiments of the present invention.
Figure 3B:
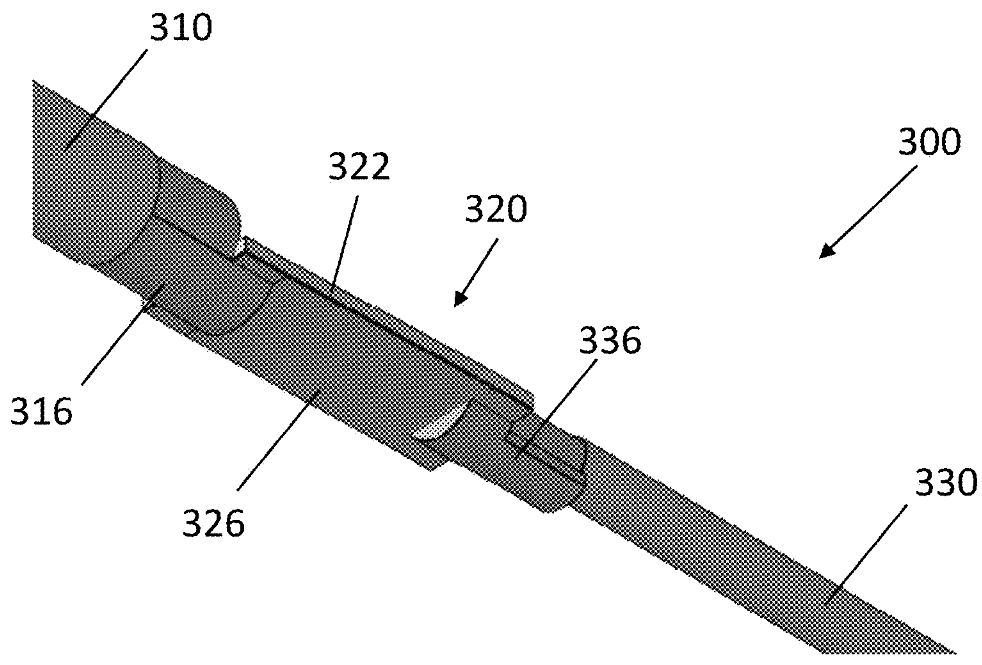

FIGS. 3A and 3B show perspective views showing the upper side and the lower side, respectively, of another coaxial cable assembly 300 which may be used in embodiments of the present invention. For example, the coaxial cable assembly 300 may be used in the electrosurgical assembly 100 described above with respect to FIG. 1. The coaxial cable assembly 300 comprises a first cable section 310, a second cable section 330, and a microstrip transmission line 320 which joins the first cable section 310 and the second cable section 330.

Although not shown in detail in FIGS. 3A and 3B, the first cable section 310 and the second cable section 330 each comprise a respective inner conductor, outer conductor coaxial with the inner conductor, and a dielectric material separating the inner conductor from the outer conductor. In a similar manner as described above with respect to FIG. 2, the first cable section 310 extends from an interface joint at its proximal end, and is configured to convey RF and/or microwave EM energy for electrosurgery. The second cable section 330 is configured to connect to an electrosurgical instrument, such as a radiating tip in the form of an RF and/or microwave antenna, for treating tissue at its distal end, and has a smaller diameter than the first cable section 310 in order to fit through the working channel of a scoping device such as an endoscope. The larger diameter of the first cable section 310 reduces losses in energy delivered to the electrosurgical instrument compared with an arrangement wherein the entire length of the coaxial cable between the interface joint and the distal tip has the same diameter which is suitable for insertion through a working channel. For example, the first cable section 310 has an outer diameter of 2.3 mm and the second cable section has an outer diameter of 1.1 mm, though other diameters may be selected to reduce losses in the first cable section 310 or dimension the section cable section 330 to fit within other working channel diameters, for example. The first cable section 310 and the second cable section 330 may have the same dimensions as the cable sections described above with respect to FIG. 2.

In contrast with the arrangement described above with respect to FIG. 2, in the coaxial cable assembly 300, the first cable section 310 and the second cable section 330 are connected by a microstrip transmission line 320. The microstrip 220 comprises a dielectric substrate 322, for example formed of a ceramic material or a PTFE composite, provided as a planar substrate, with a conductive strip 324 on an upper surface of the substrate 322 and a ground plane 326 covering a lower surface of the substrate 322. The conductive strip 324 and the ground plane 326 are each formed of a metal material, such as copper or silver plated copper. An example of a suitable material for manufacturing the dielectric substrate 322 is an RT/duroid® 5880 laminate, which may have a dielectric constant of 2.2.

As shown in FIG. 3A, an inner conductor 312 of the first cable section 310 is connected to the conductive strip 324 at a proximal end of the microstrip 320 and an inner conductor 322 of the second cable section 330 is connected to the conductive strip 324 at a distal end of the microstrip 320. For example, the inner conductors may each be soldered to the conductive strip 324 in order to ensure good conductive and mechanical connection.

As shown in FIG. 3B, an outer conductor of the first cable section 310 is connected to the ground plane 326 by a first ground plane connector 316. In some examples the first ground plane connector 316 may comprise a portion of the outer conductor which extends beyond the distal end of the dielectric of the first cable section 310 and is electrically and mechanical connected (e.g. soldered) to the ground plane 326. In other examples, the ground plane connector 316 may be a separate component which is electrically and mechanically (e.g. soldered) to each of the ground plane 326 and the outer conductor of the first cable section 310. In a similar manner, an outer conductor of the second cable section 330 is connected to the ground plane 326 by a second ground plane connector 336, which may also be formed from the outer conductor of the second cable section 330 or as a separate component.

The microstrip transmission line 320 is configured to match the impedances of the first cable section 310 and the second cable section 330 in order to reduce losses (e.g. reflective losses) at the interface between the first cable section 310 and the second cable section 330, and in particular the respective interfaces between the first cable section 310 and the transition portion 320, and between the interface portion 320 and the third cable section 330. Configuring the microstrip transmission line 320 may comprise configuring the thickness and/or width of the conductive strip 324, and may further comprise configuring the thickness of the dielectric substrate 322 in order to give the desired impedance for the microstrip 320. For example the substrate 322 may have a thickness of around 1 mm, and the conductive strip 324 a width of around 2 mm and a thickness of around 0.4 mm such that the transmission line 320 has an impedance of 50 Ω to match the impedances of the first cable section 310 and the second cable section 330.

Although not shown in FIGS. 3A and 3B, the coaxial cable assembly 300 may further comprise an outer shaft to enclose the coaxial cable assembly 300 along its length. The outer shaft may be spaced away from the coaxial cable assembly 300 in order to define a lumen or passageway outside of the assembly 300 for conveying fluid, or actuation wires for controlling functions of the electrosurgical instrument at the distal end of the cable assembly 300.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

The invention claimed is:

1. An interface joint for interconnecting an electrosurgical generator and an electrosurgical instrument, the interface joint comprising:

- a housing made of electrically insulating material, the housing having:
  - an inlet for receiving radiofrequency (RF) electromagnetic (EM) energy or microwave frequency EM energy from the electrosurgical generator, and
  - an outlet; and
- a coaxial cable assembly for connecting the outlet to the electrosurgical instrument, the coaxial cable assembly comprising a first cable section and a second cable section, wherein the first cable section has a lower loss per unit length than the second cable section;
- wherein the first cable section and the second cable section are coupled together by a transition portion, wherein the transition portion comprises a tapering section of coaxial cable in which at least one of applies:
  - an inner conductor of the tapering section of coaxial cable tapers;
  - an outer conductor of the tapering section of coaxial cable tapers; or
  - a dielectric material of the tapering section of coaxial cable tapers; and
- wherein a ratio of an inner diameter of the outer conductor to an outer diameter of the inner conductor is constant through the tapering section.

2. The interface joint according to claim 1, wherein the first cable section has a larger diameter than the second cable section.

3. The interface joint according to claim 2, wherein the first cable section has a diameter of at least 2 mm.

4. The interface joint according to claim 2, wherein the second cable section has a diameter of less than 5 mm.

5. The interface joint according to claim 1, wherein the ratio is 3.45:1.

6. The interface joint according to claim 1, wherein a length of the tapering section is no more than one eighth of a wavelength of the EM energy received from the electrosurgical generator at the inlet.

7. An interface joint for interconnecting an electrosurgical generator and an electrosurgical instrument, the interface joint comprising:

- a housing made of electrically insulating material, the housing having:
  - an inlet for receiving radiofrequency (RF) electromagnetic (EM) energy or microwave frequency EM energy from the electrosurgical generator, and
  - an outlet; and
- a coaxial cable assembly for connecting the outlet to the electrosurgical instrument, the coaxial cable assembly comprising a first cable section and a second cable section, wherein the first cable section has a lower loss per unit length than the second cable section;

wherein the first cable section and the second cable section are coupled together by a microstrip transmission line.

8. The interface joint according to claim 7, wherein the microstrip transmission line is configured to match an impedance of the first cable section and the second cable section.

9. The interface joint according to claim 1, further comprising an outer shaft about the coaxial cable assembly and defining a passageway therebetween.

10. An electrosurgical apparatus comprising:

an electrosurgical generator configured to generate radiofrequency (RF) electromagnetic (EM) energy or microwave frequency EM energy;

an electrosurgical instrument configured to deliver RF or microwave frequency EM energy to tissue;

an interface joint according to claim 1; and an interface cable configured to deliver RF or microwave frequency EM energy from the electrosurgical generator to the interface joint.

11. The electrosurgical apparatus according to claim 10, further comprising a surgical scoping device having an instrument channel for receiving at least a portion of the coaxial cable assembly.

12. The electrosurgical apparatus according to claim 11, wherein only the second cable section of the coaxial cable assembly is configured to be received within the instrument channel.

13. The electrosurgical apparatus according to claim 12, wherein an outer diameter of the first cable section is greater than a diameter of the instrument channel of the surgical scoping device.

14. The electrosurgical apparatus according to claim 11, wherein a length of the second cable section is at least a same as the length of the instrument channel of the surgical scoping device.

15. The interface joint according to claim 7, wherein the microstrip transmission line comprises a ground plane, and wherein an outer conductor of the first cable section is connected to the ground plane by a first ground plane conductor, wherein the first ground plane conductor comprises a portion of the outer conductor of the first cable section that extends beyond a distal end of a dielectric of the first cable section and is electrically and mechanically connected to the ground plane.

16. The interface joint according to claim 15, wherein an outer conductor of the second cable section is connected to the ground plane by a second ground plane conductor, wherein the second ground plane conductor comprises a portion of the outer conductor of the second cable section that extends beyond a proximal end of a dielectric of the second cable section and is electrically and mechanically connected to the ground plane.

17. The interface joint according to claim 7, wherein the microstrip transmission line, the first cable section and the second cable section each have an impedance of 50 Ω.

* * * * *